(12) United States Patent
Lee et al.

(10) Patent No.: US 9,461,157 B2
(45) Date of Patent: Oct. 4, 2016

(54) NANOWIRE ELECTRIC FIELD EFFECT SENSOR HAVING THREE-DIMENSIONAL STACKING STRUCTURE NANOWIRE AND MANUFACTURING METHOD THEREFOR

(71) Applicant: POSTECH ACADEMY—INDUSTRY FOUNDATION, Pohang-si, Gyeongsangbuk-do (KR)

(72) Inventors: Jeong Soo Lee, Pohang-si (KR); Yoon Ha Jeong, Pohang-si (KR); Sung Ho Kim, Pohang-si (KR); Ki Hyun Kim, Ulsan (KR); Tai Uk Rim, Pohang-si (KR); Chang Ki Baek, Pohang-si (KR)

(73) Assignee: POSTECH ACADEMY-INDUSTRY FOUNDATION, Pohang-Si, Gyeongsangbuk-Do (KR)

( * ) Notice: Subject to any disclaimer, the term of this patent is extended or adjusted under 35 U.S.C. 154(b) by 0 days.

(21) Appl. No.: 14/648,969

(22) PCT Filed: Nov. 22, 2013

(86) PCT No.: PCT/KR2013/010655
§ 371 (c)(1),
(2) Date: Jun. 2, 2015

(87) PCT Pub. No.: WO2014/088244
PCT Pub. Date: Jun. 12, 2014

(65) Prior Publication Data
US 2015/0303289 A1    Oct. 22, 2015

(30) Foreign Application Priority Data

Dec. 5, 2012    (KR) .......................... 10-2012-0140109

(51) Int. Cl.
*H01L 31/00*    (2006.01)
*H01L 29/775*    (2006.01)
(Continued)

(52) U.S. Cl.
CPC ......... *H01L 29/775* (2013.01); *G01N 27/4146* (2013.01); *H01L 29/66439* (2013.01); *G01N 27/4145* (2013.01)

(58) Field of Classification Search
None
See application file for complete search history.

(56) References Cited

U.S. PATENT DOCUMENTS

| | | | |
|---|---|---|---|
| 2008/0135949 A1* | 6/2008 | Lo .......................... | B82Y 10/00 257/401 |
| 2010/0283031 A1* | 11/2010 | Kim .................. | G01N 33/5432 257/9 |
| 2011/0045466 A1* | 2/2011 | Lin ...................... | C12Q 1/6804 435/29 |

FOREIGN PATENT DOCUMENTS

| JP | 2000-241343 | 9/2000 |
|---|---|---|
| JP | 2008-277814 | 11/2008 |

(Continued)

OTHER PUBLICATIONS

Written Opinion with English translation for International Application No. PCT/KR2013/010655, dated Jan. 28, 2014.

(Continued)

*Primary Examiner* — Thomas L Dickey
*Assistant Examiner* — Herve Assouman
(74) *Attorney, Agent, or Firm* — Kile Park Reed & Houtteman PLLC

(57) ABSTRACT

The present invention provides a nanowire sensor comprising nanowires, in which the nanowires are stacked to form a three-dimensional structure so that they have a large exposed surface area compared to that of a conventional straight nanowire sensor in the same limited area, thereby increasing the probability of attachment of a target material to the nanowires to thereby increase the measurement sensitivity of the sensor. Thus, a change in the electrical conductivity (conductance or resistance) of the nanowires can be sensed with higher sensitivity, suggesting that the sensor has increased sensitivity.

17 Claims, 13 Drawing Sheets

(51) Int. Cl.
*H01L 29/66* (2006.01)
*G01N 27/414* (2006.01)

(56) References Cited

FOREIGN PATENT DOCUMENTS

| KR | 10-2008-0082858 | 9/2008 |
| KR | 10-1015498 | 2/2011 |
| KR | 10-1058369 | 8/2011 |

OTHER PUBLICATIONS

International Search Report for International Application No. PCT/KR2013/010655, dated Jan. 28, 2014.

\* cited by examiner

NANOWIRE ELECTRIC FIELD EFFECT SENSOR HAVING THREE-DIMENSIONAL STACKING STRUCTURE NANOWIRE AND MANUFACTURING METHOD THEREFOR

TECHNICAL FIELD

The present invention relates to a field effect sensor comprising nanowires, and more particularly, to a nanowire field effect sensor comprising nanowires having a three-dimensional stacked structure, in which the nanowires are stacked on a substrate in a direction perpendicular to the substrate so that a larger sensing area can be obtained in a limited substrate area.

BACKGROUND ART

Electrochemical sensors are devices that change the electrochemical properties of the material to be changed to electrical signals. Electrochemical sensors are expected to be widely used as biosensors and chemical sensors depending on the kind of target material to be sensed.

For the detection and analysis of a material by an electrochemical sensor, the electrochemical sensor should is required to have high sensitivity so that a great change in the signal thereof can appear even when the target material have fine electrochemical properties. Further, the area of the electrochemical sensor, to which the target material can be attached, is required to be maximized so that a larger amount of the target material can be attached to the electrochemical sensor. In addition, for cost-effectiveness and utility, the electrochemical sensor should be fabricated to have a structure easy to mass-produce.

In such terms, nanowire field effect sensors fabricated using conventional top-down semiconductor processes are most suitable for the above-described requirements of electrochemical sensors. Among them, a nanowire channel is a one-dimensional structure, and has been proposed as a structure that has a high ability to control a gate and that can achieve high sensitivity at a high volume-to-area ratio compared to a flat channel.

To drive the nanowire field effect sensor, a detector material is attached onto the nanowire so that the target material will bind selectively thereto, and sensing is performed based on the charge of the target material. In order to effectively sense the charge of the target material, the area for capturing the target material should be large, and thus the length of the nanowire should be sufficiently long. However, because the nanowire channel is a one-dimensional structure, it is sensitively influenced by traps present in the nanowire and a gate insulating layer covering the nanowire, and thus it is difficult to maintain the difference in properties between the nanowires at a constant level, and this difficulty becomes more severe as the length of the nanowires increases.

In addition, because the nanowires have high channel resistance, the quantity of driving current decreases if the number of the nanowires connected in parallel with one another is small. Thus, when a measurement circuit for sensing is constructed, a high measurement resolution is required.

FIG. 1 illustrates an example of a conventional nanowire sensor comprising a nanowire.

Referring to FIG. 1, in the conventional nanowire sensor, a detector material is attached to a gate insulating layer on a nanowire 20 formed between a source electrode S and a drain electrode D. Next, sensing is performed based on the change in electrical conductivity of the nanowire channel by the charge of a target material which is attached selectively to the detector material. Herein, a separate submerged gate electrode 31 may also be fabricated and used to fix the potential of a solution.

The conventional nanowire sensor has a structure in which the straight nanowire is connected to the source S and the drain D. Herein, the nanowire is constructed as a single layer either attached to the upper surface of a substrate or spaced at a certain distance from the upper surface of the substrate. The sensing area of the nanowire sensor is limited to the upper, lower and side portions of the nanowire, and the size thereof is only a few square microns to a few square nanometers. To increase the sensing area of the nanowires, the number of the nanowires is required to be increased, and the area of elements per substrate area is also increased. This causes a problem in that the number of elements per substrate area decreases.

DISCLOSURE

Technical Problem

It is an object of the present invention to provide a nanowire sensor comprising nanowires, in which the nanowires are stacked to form a three-dimensional structure so that they have a large exposed surface area compared to that of a conventional straight nanowire sensor in the same limited area, thereby increasing the probability of attachment of the target material to the nanowires to thereby increase the measurement sensitivity of the sensor.

Technical Solution

To achieve the above object, in accordance with an embodiment of the present invention, there is provided a nanowire field effect sensor comprising nanowires having a three-dimensional stacked structure, the sensor comprising: a source (S) electrode formed of a semiconductor channel layer 12 and a sacrificial layer 13; a drain (D) electrode formed of the semiconductor channel layer 12 and the sacrificial layer 13; nanowires connected to one side of the semiconductor layer 12 of the source (S) electrode and to one side of the semiconductor channel layer 12 of the drain (D) electrode; and a detector material 40 which is fixed to the side of the nanowires and reacts selectively with a target material 41 introduced from the outside.

In accordance with another embodiment of the present invention, there is provided a nanowire field effect sensor comprising nanowires having a three-dimensional stacked structure, the sensor comprising: one or more semiconductor channel layers 12 and sacrificial layers 13 formed alternately on a substrate; two or more nanowire layers stacked on the substrate in a vertical direction and formed by etching the semiconductor channel layers 12 and the sacrificial layers 13 in the patterned portion of the semiconductor channel layers 12 and the sacrificial layers 13, and then selectively etching a support layer and the sacrificial layers in a portion excluding the patterned portion; a source (S) electrode formed by alternately stacking the semiconductor channel layers 12 and the sacrificial layers 13; a drain (D) electrode formed by alternately stacking the semiconductor channel layers 12 and the sacrificial layers 13; and a detector material 40 which is fixed to one side of the nanowire layers and reacts selectively with a target material 41 introduced from the outside.

Advantageous Effects

The nanowire sensor comprising nanowires having a three-dimensional stacked structure according to the present invention has a larger sensing area compared to a conventional nanowire sensor having a two-dimensional nanowire structure in the same limited area. Thus, the probability of attachment of a target material to the nanowires of the sensor of the present invention can be increased, and the change in electrical conductivity (conductance or resistance) by the attached target material can be sensed with higher sensitivity, suggesting that the sensor has increased sensitivity.

In addition, a medium is filled in the upper, side and lower portions of the nanowire layer, and thus the element is operated like GAA (gate-all-around) FETs. Thus, the ability of the nanowires to control the gate is increased to the increase the sensitivity of the sensor.

The term "GAA (gate-all-around)" means that all the four sides of the nanowire layer are used as a gate electrode 31, and the detailed description thereof is omitted herein, because it is obvious to those skilled in the art.

In addition, due to the influence of the nanowires disposed in parallel, a nanowire having high electrical conductivity influences the entire element. Accordingly, the on-state characteristics of the element are influenced mainly by a nanowire having excellent performance among the nanowires connected in parallel so that the average on-state characteristics of the element will be improved.

MODE FOR INVENTION

Hereinafter, exemplary embodiments of the present invention will be described in detail with reference to the accompanying drawings.

Figure 2:
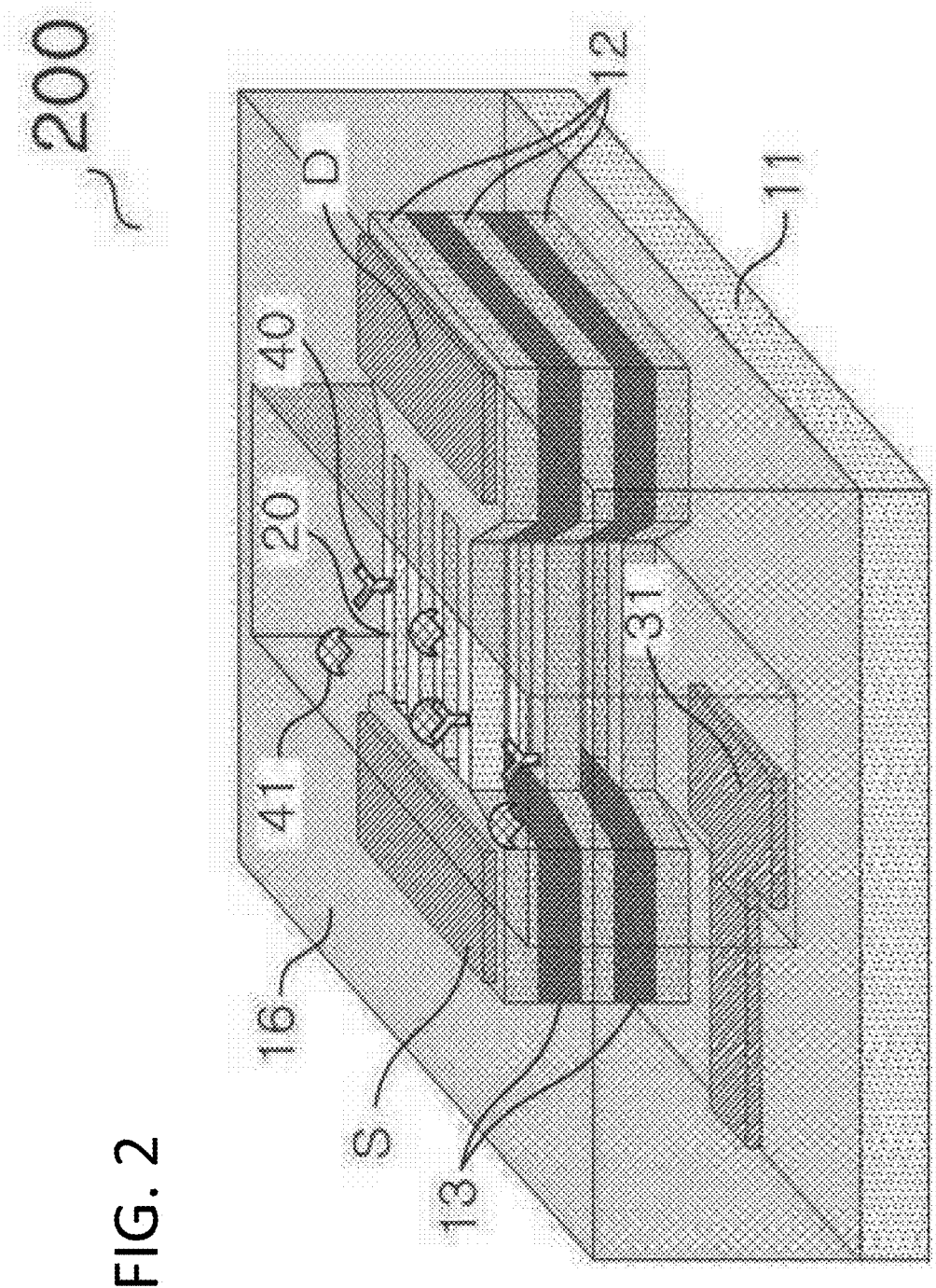
FIG. 2 illustrates the structure of a nanowire structure having a three-dimensional stacked nanowire structure according to the present invention.

FIG. 2 illustrates the structure of a nanowire sensor having a three-dimensional stacked nanowire structure according to the present invention.

Referring to FIG. 2, the nanowire sensor having a three-dimensional stacked nanowire structure according to the present invention is fabricated using a semiconductor stack of a semiconductor channel layer 12 and a sacrificial layer 13 made of either a dielectric material or a semiconductor that can be etched selectively with respect to the channel layer. In the semiconductor stack, the channel layer 12 and sacrificial layer 13 in a patterned nanowire portion are etched, and then the sacrificial layer 13 in the nanowire portion is selectively etched so that the interlayer contact between the nanowires will not occur. Herein, the layers of each of the source S and the drain D should be electrically connected with each other. If the sacrificial layer 13 is made of a dielectric material, a conductive via 32 is formed in each of the source S and the drain D to connect the layers to each other, and if the channel layer is made of silicon and the sacrificial layer 13 is made of a semiconductor material such as a silicon germanium compound, which can be etched selectively with respect to silicon, ions are selectively implanted into the source S and the drain D to increase the electrical conductivity to thereby connect the layers with each other.

Figure 1:
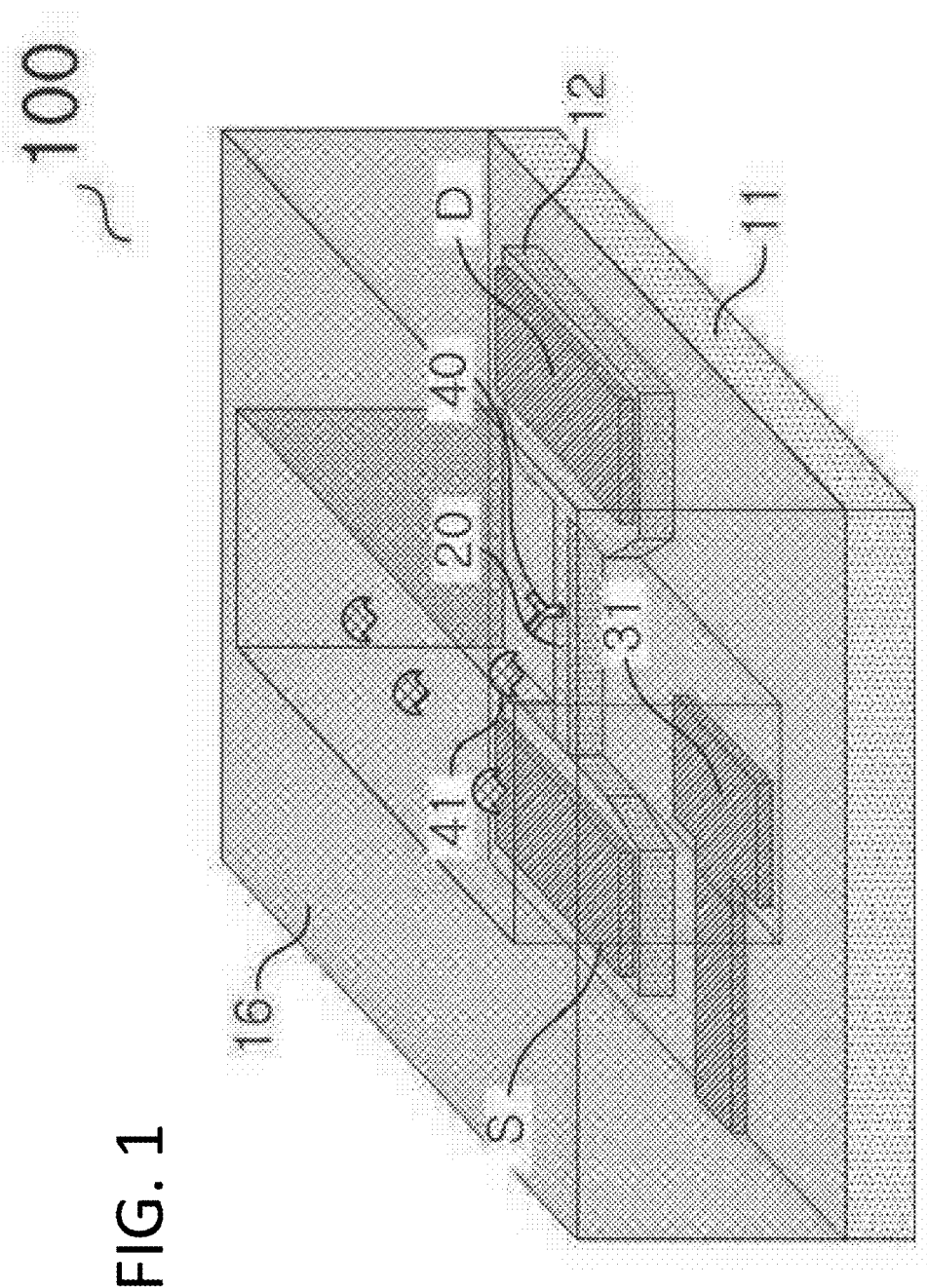
FIG. 1 illustrates the structure of a conventional nanowire sensor.

The nanowire sensor having a three-dimensional stacked nanowire structure as shown in FIG. 2 differs from the conventional nanowire sensor of FIG. 1 in that several nanowire layers stacked in a direction perpendicular to the substrate 10 can be formed by stacking one or more sacrificial layers 13 made of a material, which can be etched selectively with respect to the channel layer 12, alternately with the channel layer 12, and other elements are the same between the two sensors. Thus, in the case of the three-dimensional stacked nanowire structure, a larger number of the nanowires compared to that of conventional nanowires in the same limited area can be connected in parallel with one another.

Figure 3:
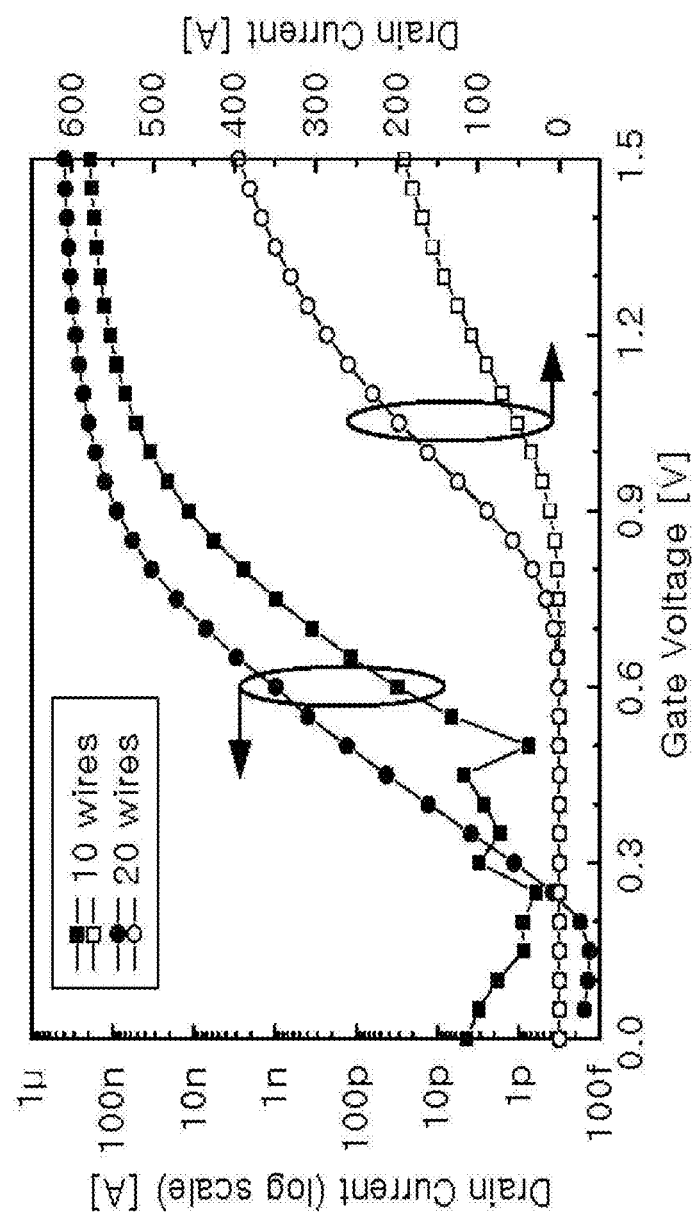
FIG. 3 shows electron microscope images of nanowire elements connected in parallel with one another and transfer characteristic curves of elements having varying numbers of nanowires.

FIG. 3 shows electron microscope images of nanowire elements connected in parallel with one another and transfer characteristic curves of elements having varying numbers of nanowires.

Referring to the measurement results in FIG. 3, the element having 20 nanowires shows a higher threshold and sub-threshold swing (SS) and a higher on-state current compared to the element having 10 nanowires. 13 and 19 threshold voltages, SSs and on-state currents for the element having 10 nanowires and the element having 20 nanowires, respectively, were averaged. As a result, it was shown that the threshold voltage of the element having 10 nanowires was as low as 80 mV, the SS was calculated to be 140 mV/dec to 123 mV/dec, and a 2-fold difference in the current was observed.

Specifically, when a plurality of nanowires having different characteristics and connected parallel with one another are used, a channel having high conductivity among the channels connected in parallel with one another has a major effect on the entire circuit, and thus an element having good on-state characteristics among the connected nanowires has a major effect to improve the on-state characteristics of the entire elements.

Meanwhile, when the number of nanowires connected in parallel in a single element increases, the sensing area, to which the target material 41 can be attached to cause a change in the electrical conductivity, increases, thereby increasing the probability of attachment of the target material 41. In addition, as the nanowires are connected in parallel with one another, the total channel area increases to increase the current, thereby eliminating the need to increase the measurement resolution of the measurement device.

Figure 4:
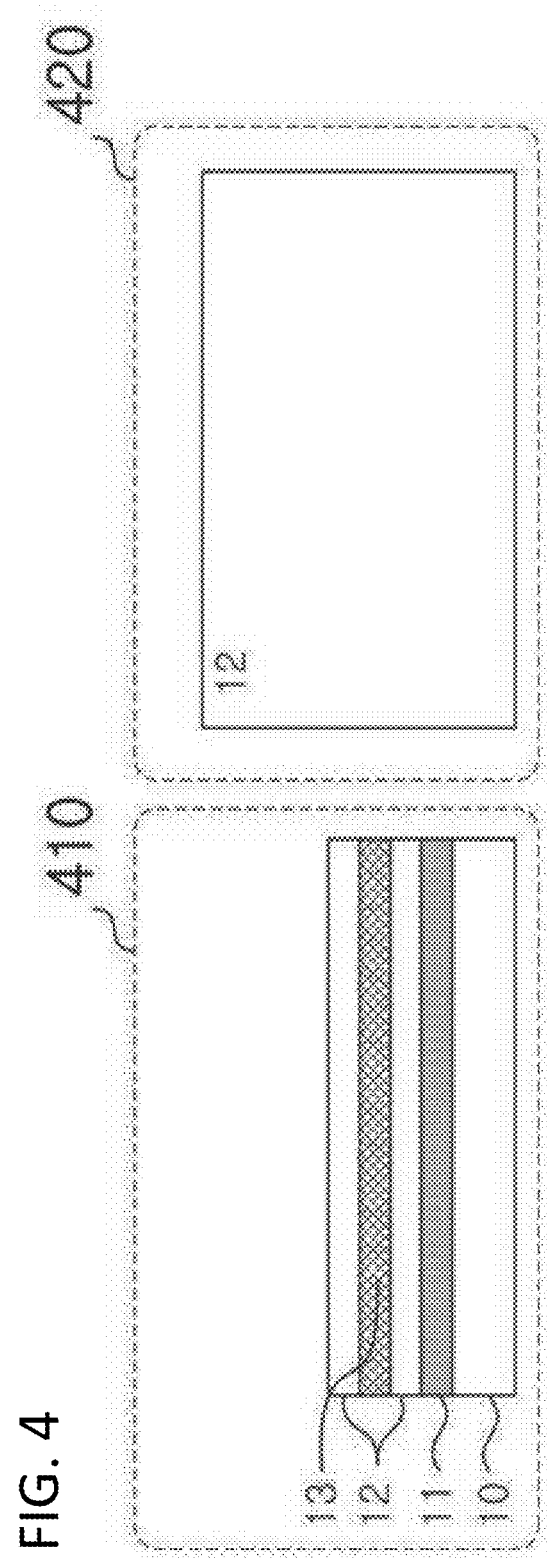
FIG. 4 shows a step of sequentially forming a channel layer and a sacrificial layer made of a dielectric material or a semiconductor material, which can be etched selectively with respect to the channel layer, on a substrate to form a multilayer structure, in a method of fabricating a nanowire sensor having a three-dimensional stacked nanowire structure according to an embodiment of the present invention.

FIG. 4 shows a step of sequentially forming a channel layer and a sacrificial layer made of a dielectric material or a semiconductor material, which can be etched selectively with respect to the channel layer, on a substrate to form a multilayer structure, in a method of fabricating a nanowire sensor having a three-dimensional stacked nanowire structure according to an embodiment of the present invention.

As shown in FIG. 4, an insulating layer 11 made of silicon oxide or silicon nitride is formed on a substrate 10. On the insulating layer 11, channel layers 12 doped at low concentration, and sacrificial layers 13 made of either a dielectric material or a semiconductor that can be etched selectively with respect to the channel layers, are formed with one another. The number of the layers stacked can be controlled.

Figure 5:
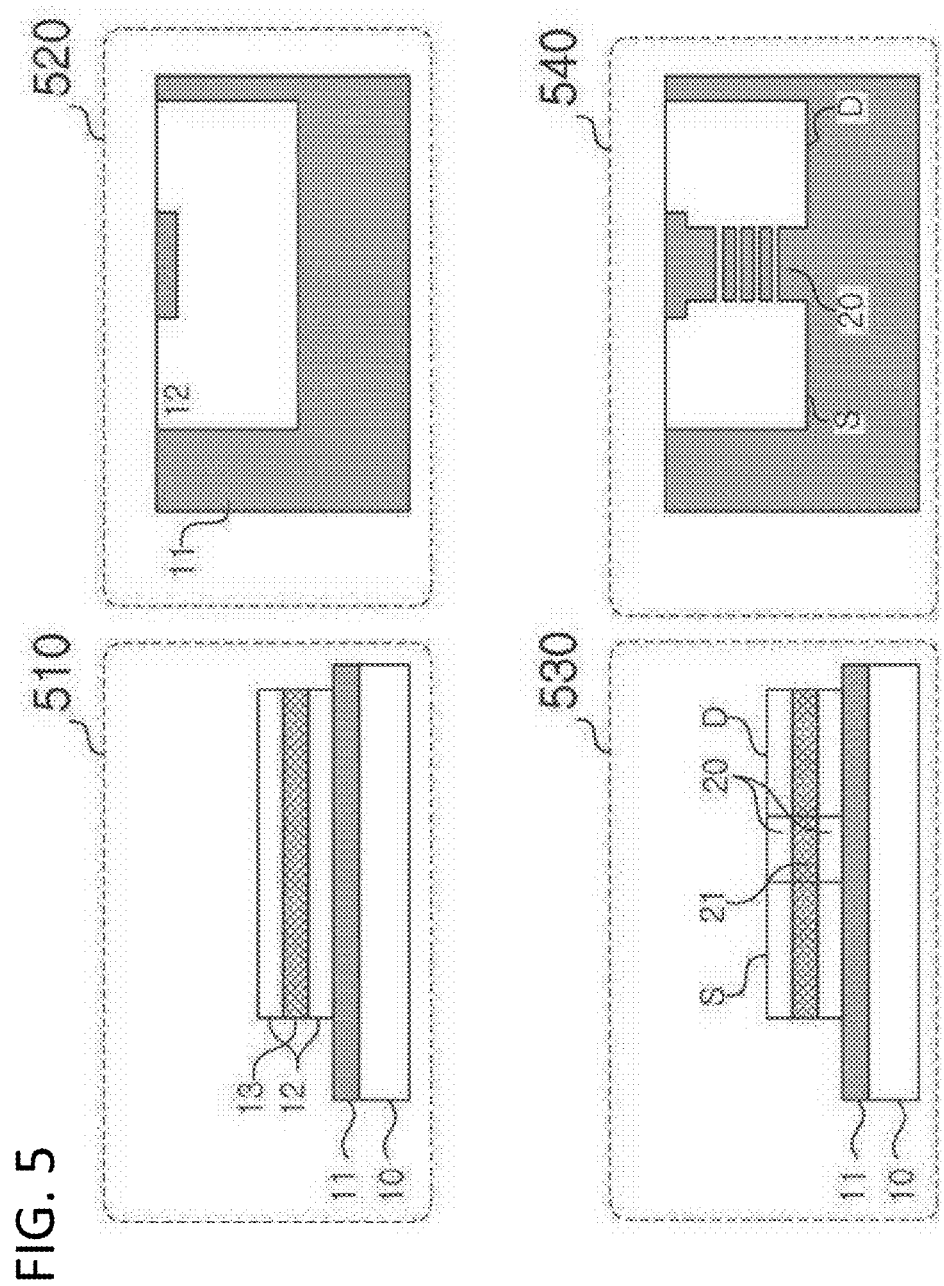
FIG. 5 shows a step of forming a source electrode, a drain electrode and a nanowire pattern on the channel layer by a lithographic process, in the method of fabricating the nanowire sensor having a three-dimensional stacked nanowire structure according to the embodiment of the present invention.

FIG. 5 shows a step of forming a source electrode, a drain electrode and a nanowire pattern on the channel layer by a lithographic process, in the method of fabricating the nanowire sensor having a three-dimensional stacked nanowire structure according to the embodiment of the present invention.

Referring to FIG. 5, an active region including a source S, a drain D and nanowires is formed by patterning using a lithographic process, followed by an etching process. The nanowires may be formed by a one-step process of forming the source S and the drain D, or may be formed by a two-step process comprising patterning the source S and the drain D and separately patterning only a nanowire portion.

Figure 6:
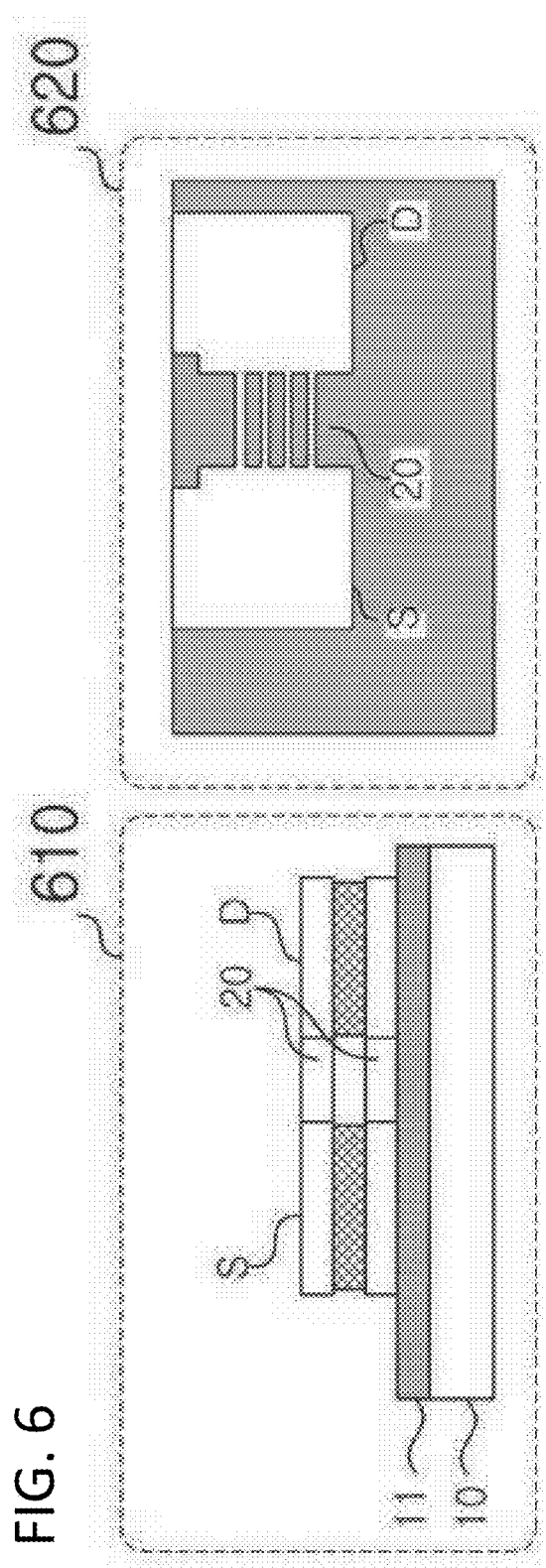
FIG. 6 shows a step of removing a support layer under the nanowires and the sacrificial layer by a wet etching process, in the method of fabricating the nanowire sensor having a three-dimensional stacked nanowire structure according to the embodiment of the present invention.

FIG. 6 shows a step of removing a support layer under the nanowires and the sacrificial layer by a wet etching process, in the method of fabricating the nanowire sensor having a three-dimensional stacked nanowire structure according to the embodiment of the present invention.

Referring to FIG. 6, the sacrificial layer 21 of the nanowire channel is removed by a wet-etching process. Herein, the etching is performed using an anisotropic wet-etching process, and an etching solution having a high etch selectivity between the sacrificial layer material and the channel layer material should be used to selectively etch the sacrificial layer without etching the channel layer.

Figure 7:
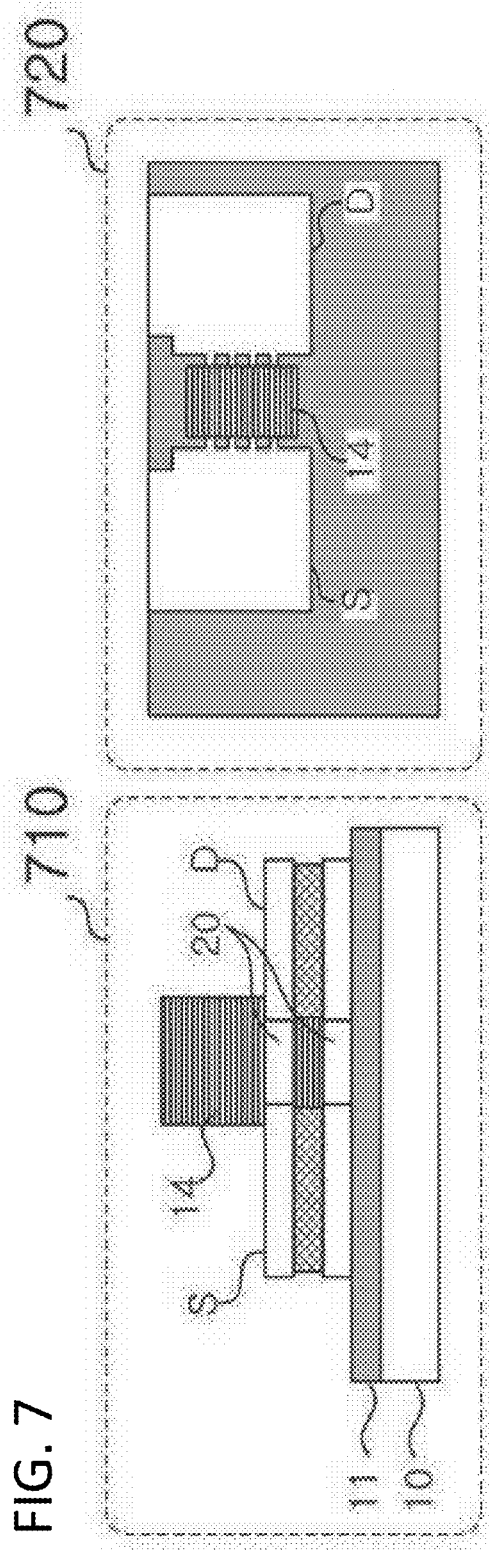
FIG. 7 shows a step of implanting ions into the source electrode and the drain electrode, in the method of fabricating the nanowire sensor having a three-dimensional stacked nanowire structure according to the embodiment of the present invention.

FIG. 7 shows a step of implanting ions into the source electrode and the drain electrode, in the method of fabricating the nanowire sensor having a three-dimensional stacked nanowire structure according to the embodiment of the present invention.

Referring to FIG. 7, if the channel layer is made of silicon and the sacrificial layer 13 is made of a semiconductor material such as a silicon germanium compound, which can be etched selectively with respect to silicon, ion implantation is performed to increase the electrical conductivity of the source S and the drain D to thereby connect the layers of each of the source S and drain D with each other. In the ion implantation process, an ion implantation preventing film 14 is preferably used to prevent ions from penetrating the channel layer 20 of the nanowire, and ions are preferably implanted at high concentration.

Figure 8:
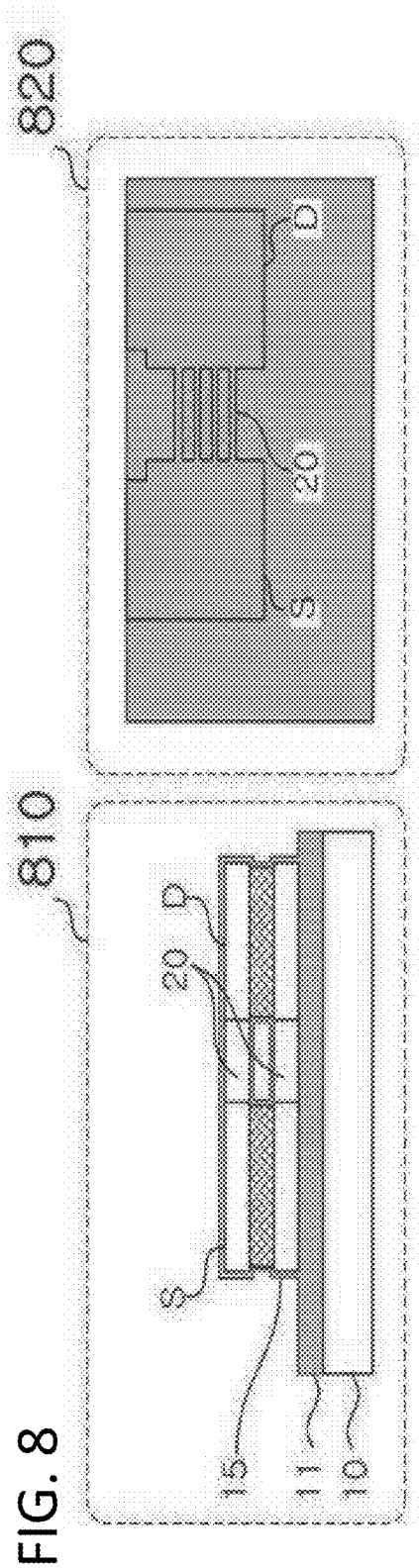
FIG. 8 shows a step of forming a gate insulating layer on the outer surfaces of the source electrode, the drain electrode and the nanowires, in the method of fabricating the nanowire sensor having a three-dimensional stacked nanowire structure according to the embodiment of the present invention.

FIG. 8 shows a step of forming a gate insulating layer on the outer surfaces of the source electrode, the drain electrode and the nanowires, in the method of fabricating the nanowire sensor having a three-dimensional stacked nanowire structure according to the embodiment of the present invention.

Referring to FIG. 8, a gate insulating layer 15 is formed on the outer surface of the nanowires to electrically insulate the nanowires from a solution outside the nanowires. On the surface of the gate insulating layer, a chemical radical required for subsequent attachment of a detector material is exposed, and a separate metal may be deposited.

The nanowire formation step, the ion implantation step, the support layer removal step and the gate insulating layer formation step may be performed in a changed order for the purposes of increasing the sensitivity of the nanowire sensor and reducing the signal-to-noise ratio.

Figure 9:
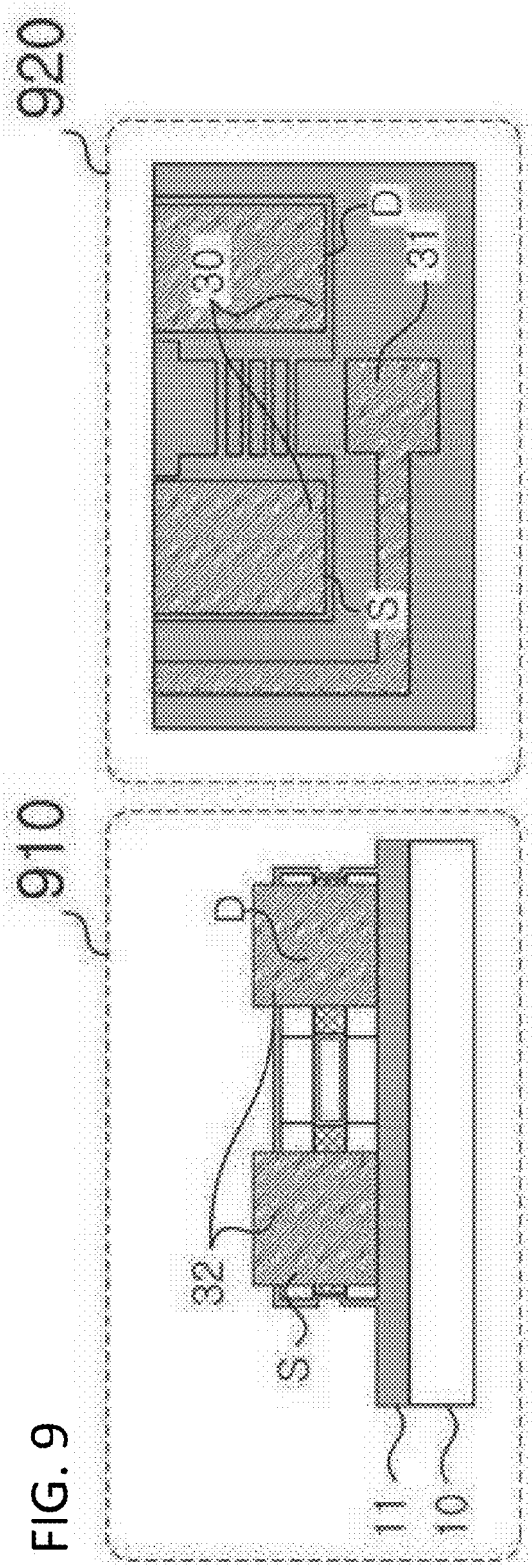
FIG. 9 shows a step of forming a metal via if the sacrificial layer is made of a dielectric material such as silicon oxide, in the method of fabricating the nanowire sensor having a three-dimensional stacked nanowire structure according to the embodiment of the present invention.

FIG. 9 shows a step of forming a metal via 32 if the sacrificial layer 13 is made of a dielectric material such as silicon oxide, in the method of fabricating the nanowire sensor having a three-dimensional stacked nanowire structure according to the embodiment of the present invention.

If the sacrificial layers 13 are made of a dielectric material such as silicon oxide, as shown in FIG. 9, a metal via 32 is formed in each of the source S and the drain D to connect the layers of each of the source S and the drain D to each other.

Figure 10:
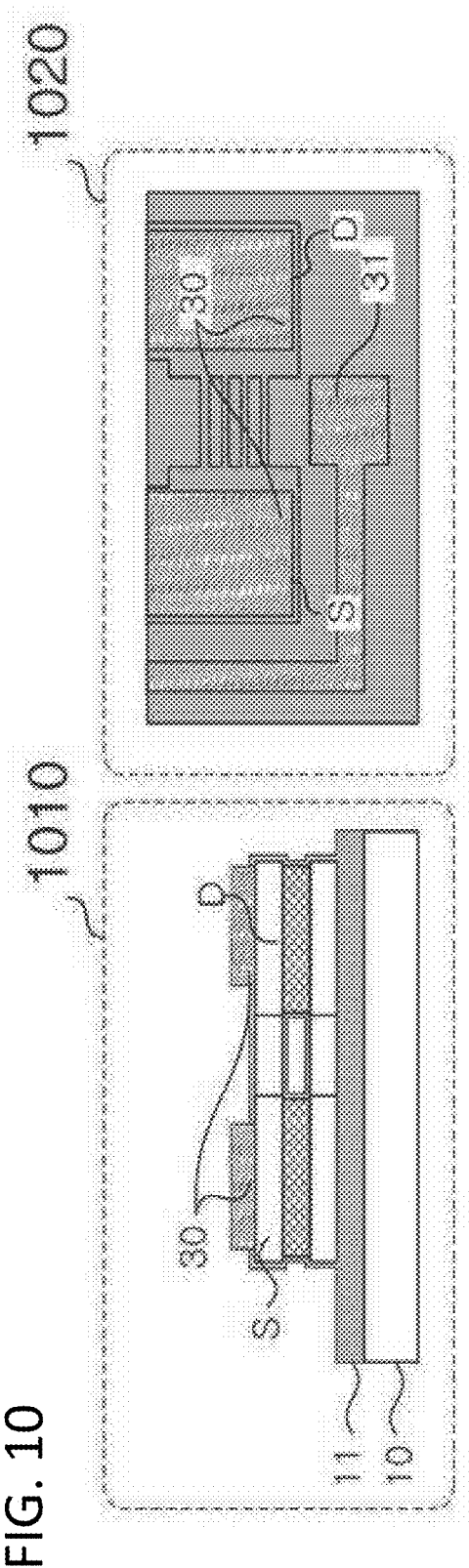
FIG. 10 shows a step of forming a metal electrode on each of the source electrode and the drain electrode, in the method of fabricating the nanowire sensor having a three-dimensional stacked nanowire structure according to the embodiment of the present invention.

FIG. 10 shows a step of forming a metal electrode on each of the source electrode and the drain electrode, in the method of fabricating the nanowire sensor having a three-dimensional stacked nanowire structure according to the embodiment of the present invention.

If the sacrificial layers 13 are made of a semiconductor that can be etched selectively with respect to the channel layer 12, the channel layers in each of the source S and the drain D are electrically connected to with each other by the process shown in FIG. 7. Thus, as shown in FIG. 10, a metal electrode layer 30 is formed on each of the source S and the drain D. Because the source S and the drain D have the gate insulating layer 15 formed thereon, a process of removing the insulating layer should be performed before formation of the metal electrode layer. In addition, a separate submerged gate electrode 31 may further be formed on the lower insulating layer 11 so that it will be exposed to a solution so as to apply potential directly to the solution.

Figure 11:
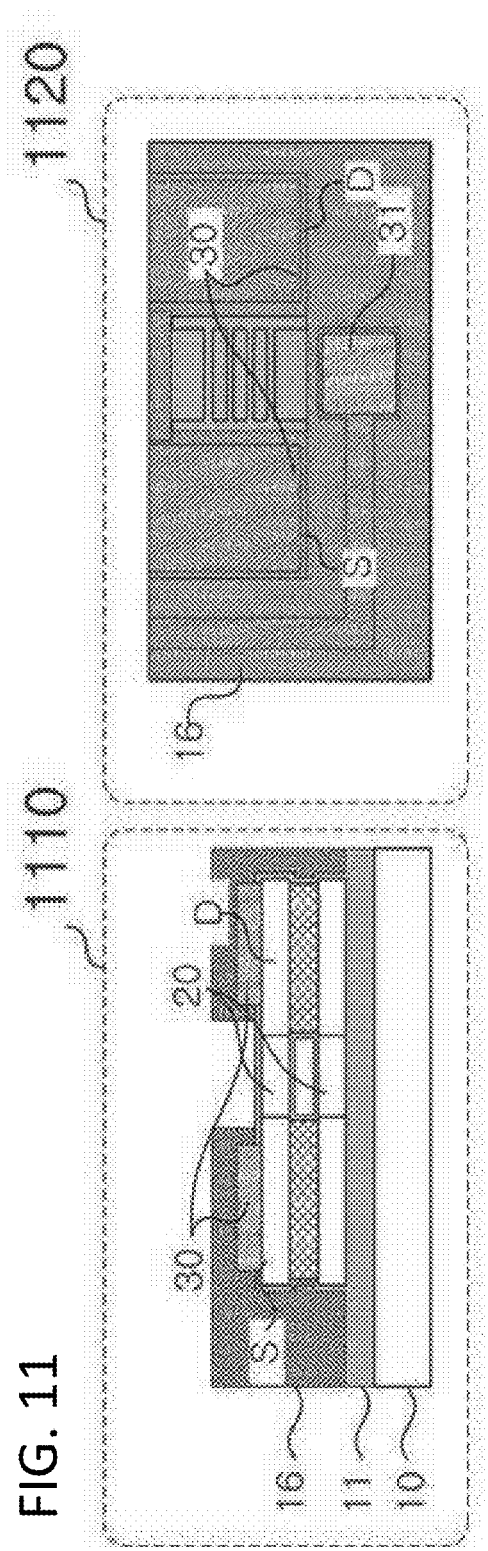
FIG. 11 shows a step of forming an additional insulating layer for insulation between a solution and the metal electrodes on the source (S), the drain (D) and a connection line between the metal electrodes, in the method of fabricating the nanowire sensor having a three-dimensional stacked nanowire structure according to the embodiment of the present invention.

FIG. 11 shows a step of forming an additional insulating layer for insulation between a solution and the metal electrodes on the source (S), the drain (D) and a connection line between the metal electrodes, in the method of fabricating the nanowire sensor having a three-dimensional stacked nanowire structure according to the embodiment of the present invention.

As shown in FIG. 11, an insulating layer 16 for insulation between a solution and the metal electrode layer 30 is additionally formed on the source S, the drain D and the connection line between the metal electrodes. Herein, the gate insulating layer of the nanowires for sensing and the submerged gate electrode are required to be exposed.

Figure 12:
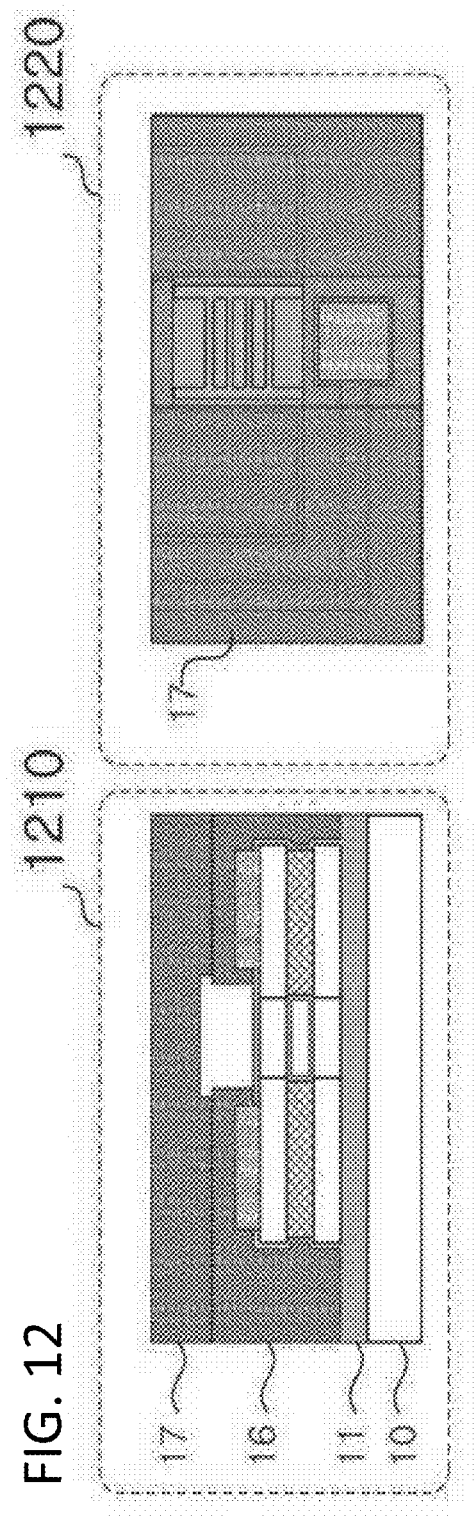
FIG. 12 shows a step of forming a channel, through which a solution can flow, between the exposed nanowire gate insulating layer and the submerged gate electrode, in the method of fabricating the nanowire sensor having a three-dimensional stacked nanowire structure according to the embodiment of the present invention.

FIG. 12 shows a step of forming a channel made of a separate material, through which a solution can flow, between the exposed nanowire gate insulating layer and the exposed submerged gate electrode, in the method of fabricating the nanowire sensor having a three-dimensional stacked nanowire structure according to the embodiment of the present invention.

As shown in FIG. 12, a fluid channel layer 17 is formed between the exposed nanowire gate insulating layer and the exposed submerged gate electrode to form a channel through which a solution can flow, thereby protecting the solution from atmospheric pollutants.

Figure 13:
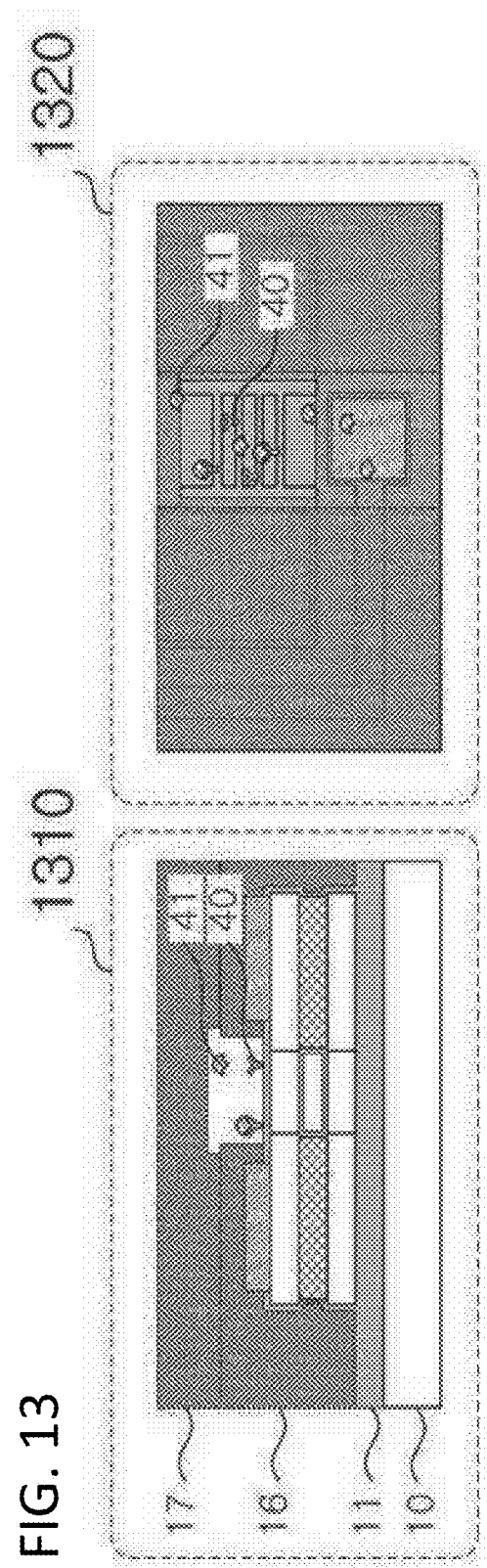
FIG. 13 shows a step of fixing, to the exposed nanowire pattern, a detector material which is react with the target material introduced from the outside, in the method of fabricating the nanowire sensor having a three-dimensional stacked nanowire structure according to the embodiment of the present invention.

FIG. 13 shows a step of fixing, to the exposed nanowire pattern, a detector material 40 which reacts with the target material 41 introduced from the outside, in the method of fabricating the nanowire sensor having a three-dimensional stacked nanowire structure according to the embodiment of the present invention.

As shown in FIG. 13, a detector material 40 is attached to the surface of the nanowire channel by use of a chemical radical, and a target material 41 is attached to the detector material 40 so that the charge of the target material 41 can influence the electrical conductivity of the nanowire channel.

The nanowire sensor according to the present invention is an element that is operated based on the electrochemical properties of the target material 41, and may comprise the sacrificial layer 13 and the semiconductor channel layer 12 doped or undoped with n-type or p-type impurity depending on the kind and electrochemical properties of target material 41.

Although the preferred embodiments of the present invention have been described for illustrative purposes, those skilled in the art will appreciate that various modifications, additions and substitutions are possible, without departing from the scope and spirit of the invention as disclosed in the accompanying claims.

The invention claimed is:

1. A nanowire field effect sensor comprising nanowires having a three-dimensional stacked structure, the nanowire field effect sensor comprising:
   a substrate for forming the nanowire field effect sensor;
   a source electrode formed by alternately stacking one or more semiconductor channel layers and sacrificial layers on one side of the substrate in a direction perpendicular to the substrate;
   a drain electrode formed by alternately stacking one or more semiconductor channel layers and sacrificial layers on another side of the substrate in a direction perpendicular to the substrate;
   one or more nanowires connected between the semiconductor channel layers of the source electrode and the semiconductor channel layers of the drain electrode and stacked in a direction perpendicular to the substrate;
   a channel made of a separate material through which a solution can flow and formed between a rate insulating layer of an outer surface of the nanowires and a submerged gate electrode formed on the substrate; and
   a detector material which is fixed to a side of the nanowires and reacts selectively with a target material introduced from an outside source.

2. The nanowire field effect sensor of claim 1, wherein the nanowires have a width ranging from 1 nm to 10 μm.

3. The nanowire field effect sensor of claim 1, wherein the nanowires are spaced at a predetermined distance from the substrate in a direction perpendicular to the substrate.

4. The nanowire field effect sensor of claim 1, wherein one or more of the nanowires are connected in parallel with one side of the semiconductor channel layers of the source electrode and with one side of the semiconductor layers of the drain electrode, and the nanowires connected in parallel form two or more alternating layers.

5. The nanowire field effect sensor of claim 1, wherein a selective reaction between the detector material and the target material occurs on all sides of the nanowires.

6. The nanowire field effect sensor of claim 1, wherein the submerged gate electrode is configured to apply potential directly to a solution containing the target material.

7. The nanowire field effect sensor of claim 1, wherein the substrate is used as a gate electrode to control a conductance of the nanowires.

8. The nanowire field effect sensor of claim 1, wherein a gate electrode made of the substrate and the submerged gate electrode on the substrate are simultaneously used to control a conductance of the nanowires.

9. The nanowire field effect sensor of claim 1, wherein the substrate is made of a semiconductor, polymer or non-conductor material.

10. The nanowire field effect sensor of claim 1, wherein the sacrificial layers are formed of a dielectric material or a semiconductor material, which are etchable selectively with respect to the semiconductor channel layers.

11. A method for fabricating a nanowire field effect sensor having a three-dimensional stacked nanowire structure, the method comprising the steps of:
    alternately forming sacrificial layers and semiconductor channel layers on a substrate to form a multilayer structure;
    forming an electrode pattern and a nanowire pattern, which comprises a single straight line or a plurality of straight lines connected in parallel with each other, on one side of the semiconductor layers by a lithographic process;
    removing a support layer for the nanowires and the sacrificial layers by an etching process;
    implanting ions into a source electrode and a drain electrode;
    forming a first gate insulating layer on outer surfaces of the source electrode, the drain electrode and the nanowires;
    forming a metal electrode on one side of each of the source electrode and the drain electrode;
    forming a second insulating layer, configured to insulate between a solution and the metal electrode, on one side of each of the source electrode, the drain electrode and a connection line between the metal electrodes;
    forming a channel between the first gate insulating layer of the nanowires and a submerged gate electrode by use of a separate material so that the solution is flowable through the channel; and
    fixing, to the nanowire pattern, a detector material which is to react with a target material introduced from an outside source.

12. The method of claim 11, wherein the removing step comprises removing the support layer and the sacrificial layers so that a bottom of the nanowires is spaced apart from the substrate and that the nanowires are spaced apart from each other and that a fluid is capable of covering the nanowires.

13. The method of claim 11, wherein the removing step comprises subjecting the sacrificial layers of the nanowires to a wet etching process and a dry etching process, which enable selective etching.

14. The method of claim 11, wherein the fixing step comprises doping the channel of the nanowires, the source electrode and the drain electrode with n-type impurity according to electrochemical properties of the target material.

15. The method of claim 11, wherein the fixing step comprises doping the source electrode, the drain electrode and the nanowires with p-type impurity according to electrochemical properties of the target material.

16. The method of claim 11, wherein the step of forming the first insulating layer further comprises, before forming the gate insulating layer, high-temperature oxidation and a process of removing an oxide layer.

17. The method of claim 11, wherein the step of forming the electrode comprises forming a metal via, if the sacrificial layers are formed of a dielectric material selected from among oxide and nitride.

* * * * *